(12) United States Patent
Bramlet et al.

(10) Patent No.: US 6,443,954 B1
(45) Date of Patent: Sep. 3, 2002

(54) FEMORAL NAIL INTRAMEDULLARY SYSTEM

(76) Inventors: Dale G. Bramlet, 2044 Brightwaters Blvd., NE., St. Petersburg, FL (US) 33704; Patrick J. Cosgrove, 12200 4$^{th}$ St. E., Treasure Island, FL (US) 33706; John A. Sodeika, 11650 Harborside Cir., Largo, FL (US) 33773; Peter M. Sterghos, 5291 40$^{th}$ Ave., St. Petersburg, FL (US) 33709

( * ) Notice: Subject to any disclaimer, the term of this patent is extended or adjusted under 35 U.S.C. 154(b) by 0 days.

(21) Appl. No.: 09/841,851

(22) Filed: Apr. 24, 2001

(51) Int. Cl.$^7$ ................................................. A61B 17/56
(52) U.S. Cl. .............................. 606/62; 606/65; 606/72; 606/73
(58) Field of Search .............................. 606/62, 64, 65, 606/60, 63, 66, 67, 68, 70, 81, 89; 623/16.11, 17.11, 23.27

(56) References Cited

U.S. PATENT DOCUMENTS

| | | | |
|---|---|---|---|
| 4,227,518 A | 10/1980 | Aginsky | |
| 4,236,512 A | 12/1980 | Aginsky | |
| 4,275,717 A | 6/1981 | Bolesky | |
| 4,453,539 A | 6/1984 | Raftopoulos et al. | |
| 4,519,100 A | 5/1985 | Wills et al. | |
| 4,590,930 A | 5/1986 | Kurth et al. | |
| 4,632,101 A | 12/1986 | Freedland | |
| 4,721,103 A | 1/1988 | Freedland | |
| 4,862,883 A | 9/1989 | Freeland | |
| 5,032,125 A | * 7/1991 | Durham et al. | ............... 606/62 |
| 5,041,114 A | 8/1991 | Chapman et al. | |
| 5,057,103 A | 10/1991 | Davis | |
| 5,454,813 A | * 10/1995 | Lawes | ........................ 606/62 |
| 5,810,820 A | 9/1998 | Santori et al. | |
| 5,928,235 A | * 7/1999 | Friedl | .......................... 606/64 |
| 5,971,986 A | 10/1999 | Santori et al. | |
| 5,976,139 A | 11/1999 | Bramlet | |
| 6,077,264 A | 6/2000 | Chemello | |
| 6,126,661 A | 10/2000 | Faccioli et al. | |
| 6,183,474 B1 | * 2/2001 | Bramlet et al. | ............... 606/66 |
| 6,235,031 B1 | * 5/2001 | Hodgeman et al. | ........... 606/64 |

* cited by examiner

*Primary Examiner*—Pedro Philogene
(74) *Attorney, Agent, or Firm*—McHale & Slavin (57) ABSTRACT

An intramedullary system for securing portions of a bone together has a lag screw assembly extending through a radial bore in an intramedullary nail. The lag screw is inserted into one portion of a bone and deployed to fix the leading end. The intramedullary nail is placed in the intramedullary canal of a portion of the bone and the trailing end of the lag screw assembly is adjustably fixed in the radial bore to provide compression between the lag screw assembly and the intramedullary nail. The intramedullary nail has a cap screw in the proximal end holding the lag screw assembly and a tang in the distal end. The tang has legs extending through the nail to fix the distal end in the intramedullary canal.

16 Claims, 6 Drawing Sheets

FEMORAL NAIL INTRAMEDULLARY SYSTEM

FIELD OF THE INVENTION

The present invention generally relates to an intramedullary system for coupling bone portions across a fracture therebetween and, more specifically, to an intramedullary hip pinning system for rigidly interconnecting a femoral head portion to the remaining portion(s) of the femur and across a fracture or fractures in the area of the femoral neck or the shaft of the femur or combinations of such fractures.

BACKGROUND OF THE INVENTION

Bones are the hard parts of the skeleton found in vertebrates. In its most basic construct, bones are formed of a relatively soft, spongy cancellous material surrounded by a much harder cortex. The cancellous bone yields under relatively low loading, while the much more dense cortical bone supports much higher loading.

A hip joint is a heavily stressed, load-carrying bone joint in the human body. It is essentially a ball and socket joint formed by the top of the femur which rotates within a cup-shaped aceta bulum at the base of the pelvis. When a break or fracture occurs adjacent to the top of the femur, the separated portions of the femur must be held together while healing occurs.

Historically, there have been a number of techniques used for treatment of fractures of the proximal end of the femur. In early parts of this century, patients were merely placed in bed or in traction for prolonged periods, frequently resulting in deformity or death.

In the 1930s, the Smith-Peterson nail was introduced. This device was inserted into the intramedullary canal of the femur resulting in immediate fixation of hip fractures, early mobilization of the patient, and a lower morbidity and mortality. A number of nails have been introduced for fracture fixation of the femur in its proximal end, including the Jewett Nail and Enders Nail.

Intramedullary nails have been inserted down the entire length of the femoral canal to provide a basis for the fixation. Threaded wires, standard bone screws or cannulated bone screws were then inserted through or along side the proximal nail and into the femoral head to provide fixation and rotational stability. The conventional nails did not provide compression of the proximal bone fragments against each other. Also, in longer nails the distal tip of the nail tended to rotate out of plane which forced the surgeon to locate the distal screw holes using fluoroscopy by a method commonly known as "free-handing".

In the 1960s, the compression hip screw was introduced, resulting in improved fixation of the proximal femur. A lag screw assembly was inserted into the femoral head, a plate was attached to the lateral femur, and a compression screw joined the two. These implants provided a more rigid structure for the patient and allowed the surgeon to compress the fractured fragments against each other thereby decreasing the time to mobility. A number of compression hip screws have been introduced for fracture fixation about the proximal femur, including the Dynamic Hip Screw.

During implantation these compression hip screws require an incision at least equal to the length of the plate being used which extends operative time and blood loss. The side plate also creates a protuberance on the lateral side which provides an annoyance to the patient. Compression hip screw systems also fail to provide adequate compression in oseteogenic patients because the lag screw assembly threads fail to obtain sufficient purchase due to poor bone stock. Poor purchase is known to contribute to nonunion, malunion and the lag screw assembly eroding through the superior bone of the head of the femur in a condition known as "cut out". Additionally, many patients are dissatisfied with the results of compression hip screw surgery because of the excessive sliding to a medial displacement and shortening position which leads to a change in gait.

Newer devices and inventions include additions to the nail and lag screw assembly to ease or eliminate the need to locate the distal screw holes and improve the fixation. These newer devices are commonly classified as "expanding devices" and expand in size after placement to fill the intramedullary cavity. Freedland, U.S. Pat. Nos. 4,632,101, 4,862,883 and 4,721,103, Chemello, U.S. Pat. No. 6,077,264 and Davis, U.S. Pat. No. 5,057,103 describe a method of fixation which provides points which contact the internal cortical wall. In these patents a mechanism is actuated deploying arms or anchor blades through the cancellous bone to contact the inner cortical wall. These methods are complex and difficult to retract should the nail or lag screw assembly require extraction. Further, the screws do not deploy through the cortical bone.

Other expanding devices provide surface contact with the internal cortical wall resulting in a wedge effect. Kurth, U.S. Pat. No. 4,590,930, Raftopoulos, U.S. Pat. No. 4,453,539 and Aginski, U.S. Pat. No. 4,236,512, among others have described mechanisms which deploy or expand with a molly bolt concept. These methods are complex and difficult to retract should the nail or lag screw assembly require extraction and, also, do not deploy through the cortical bone.

Bolesky, U.S. Pat. No. 4,275,717 was the first to discuss engagement within the cortical wall. However, Bolesky's invention does not address controlled penetration into the wall and required permanent implantation of the actuation rod. In addition, Bolesky does not address the fundamental problem of the actuation rod's protrusion extramedullarly into the surrounding musculature.

In U.S. Pat. Nos. 5,976,139 and 6,183,474B1, Bramlet et al describe a surgical anchor which has deployable tangs. These tangs are simple in design, internally positioned, yet easily deployed into, and if desired through, the cortical bone providing improved purchase for compression of a fracture, especially in osteogenic bone. These tangs are just as easily retracted should the device require explantation.

Approximately 10 years ago Howmedica (Rutherford, N.J., United States) was the first to produce the "Gamma Nail", named for its similarity in shape to the Greek letter, and other designs soon followed. These devices combined desirable aspects of both intramedullary nails and compression hip screws. These intramedullary hip compression screws required a few small incisions, allowed capture of the most proximal fragments of the femur, rigid fixation of the most proximal and distal fragments, and a sliding lag screw assembly or anchor which fits within a barreled sleeve for allowing improved compression of the fragments as the patient ambulates and begins to bear weight on the fractured limb. The nails are typically held in place on the distal end through interference forces with the intramedullary canal and through the use of locking screws.

The Gamma Nail's shape accommodates the relative shape of the greater trochanter and femoral neck and head fragments, and the shape of the hip is therefore preserved. Nonunions are less frequent because bone-to-bone contact is maintained and the bulk of an intramedullary hip screw blocks excessive sliding. Intramedullary hip screws work best in reverse obliquity fractures, a fracture, in which compression hip screws are least effective.

Osteogenic bone still provides a poor medium for purchase of the lag screw assembly of the Gamma Nail inhibiting adequate compression and rotational stability. Longer nails continue to see the distal tip of the nail rotating out of plane forcing the surgeon tolocate the distal screw holes by the free-hand method. The free-handing technique leads to an increased surgical time and exposes the surgeon and patient to increased radiation dosages.

Clearly a need exists for a system which is superior to the, "gold standard," of compression hip screws while minimizing the surgical insult to the human body. Such a system, as disclosed and claimed herein, includes a simple, effective and controllable fixation device which allows greater purchase of the lag screw assembly within the femoral head, improved compression across the fracture line, provides a means of rotational stability both in the femoral head and in the femoral shaft, and minimizes the need for additional distal incisions to locate and place locking screws. This system allows the surgeon a choice of penetration distance within the femoral head and femoral shaft fixation based upon the injuries presented and the desired level of treatment. Finally, this system allows explantation to occur as easily as implantation.

SUMMARY OF THE INVENTION

An intramedullary nail system is provided for coupling bone portions on opposite sides of a fracture. The intramedullary nail system according to the invention is especially suitable for installation within the medullary canal of a fractured long bone, such as found in an arm or leg. In one embodiment of the present invention, the intramedullary nail system includes an elongated rod with radial portals which allow passage of locking screws or anchoring tangs and a lag screw assembly. The rod has a distal end and a proximal end with internal threads. A lag screw assembly having an externally threaded portions. The radial portals in the distal end allow passage of internally deployable and retractable anchoring tangs or cortical screws. A radial portal in the proximal end accommodates a sleeve which passes through the intramedullary nail and through which the lag screw assembly passes freely while preventing rotation of said lag screw assembly. A compression screw engages the sleeve and cooperates with the internal threads of the lag screw assembly trailing end providing axial translation of the lag screw assembly within the sleeve. The proximal end has an axial portal for an end cap with external threads on the trailing end which engages the internal threads of the intramedullary nail. The end cap has a parabaloid leading end which engages the sleeve thereby preventing translation and rotation of said sleeve.

When the intramedullary nail is placed into position the anchoring tang assembly is actuated to deploy the tangs out from their stowed position into the cortical bone. The tangs are deployed to any desired position thereby achieving a desired fixation based upon the quality of the bone.

In one embodiment, cortical screws may be placed to secure the intramedullary nail with the surrounding cortical bone. In another embodiment, the tang assembly is actuated and the tangs are deployed to any desired position thereby achieving the desired fixation based upon the quality of the bone.

The sleeve is coaxially inserted over the lag screw assembly's trailing end and through the intramedullary nail. An end cap is threaded into the intramedullary nail with it's leading end contacting and frictionally holding the sleeve. By providing interference against the sleeve, the sleeve is prevented from altering its position either through translation or rotation.

The compression screw passes through the sleeve and engages the lag screw assembly. As the compression screw is tightened the lag screw assembly and associated first bone portion are pulled against the intramedullary nail and second bone portion resulting in compressive forces being applied across the fracture.

The intramedullary nail is preferably cannulated to allow passage of one or more anchoring tang assemblies. These anchoring tang assemblies are inserted from the proximal end towards the distal end and the tangs deployed by means of an actuator driver. An alternate embodiment describes a retracted anchoring tang assembly which is permanently placed within the distal end of the intramedullary nail and is deployed or retracted by means of an actuator driver from the proximal end of the intramedullary nail.

The lag screw assembly preferably contains a permanently placed anchoring tang assembly stored in a retracted position within the leading end. The tangs are deployed or retracted from the trailing end of the lag screw assembly.

The anchoring tang assembly contains arcurate shaped tangs that are permanently attached to the assembly's main body. These tangs are initially formed into a prescribed position for storage. As the assembly is actuated, and the tangs deploy, the tangs are formed into their final shape through interaction with the portal of either the intramedullary nail or the lag screw assembly.

The compression screw preferably contains a patch of ultra-high molecular weight poly-ethylene (UHMWPE) within the threads. This provides constant positive engagement between the compression screw external threads and the lag screw assembly internal threads.

The end cap preferably contains a patch of ultra-high molecular weight poly-ethylene (UHMWPE) within the threads. This provides constant positive engagement between the end cap external threads and the intramedullary nail internal threads. In its final position the end cap exerts a force upon the sleeve which inhibits the sleeve from sliding or rotating out of a prescribed position.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION

Figure 1:
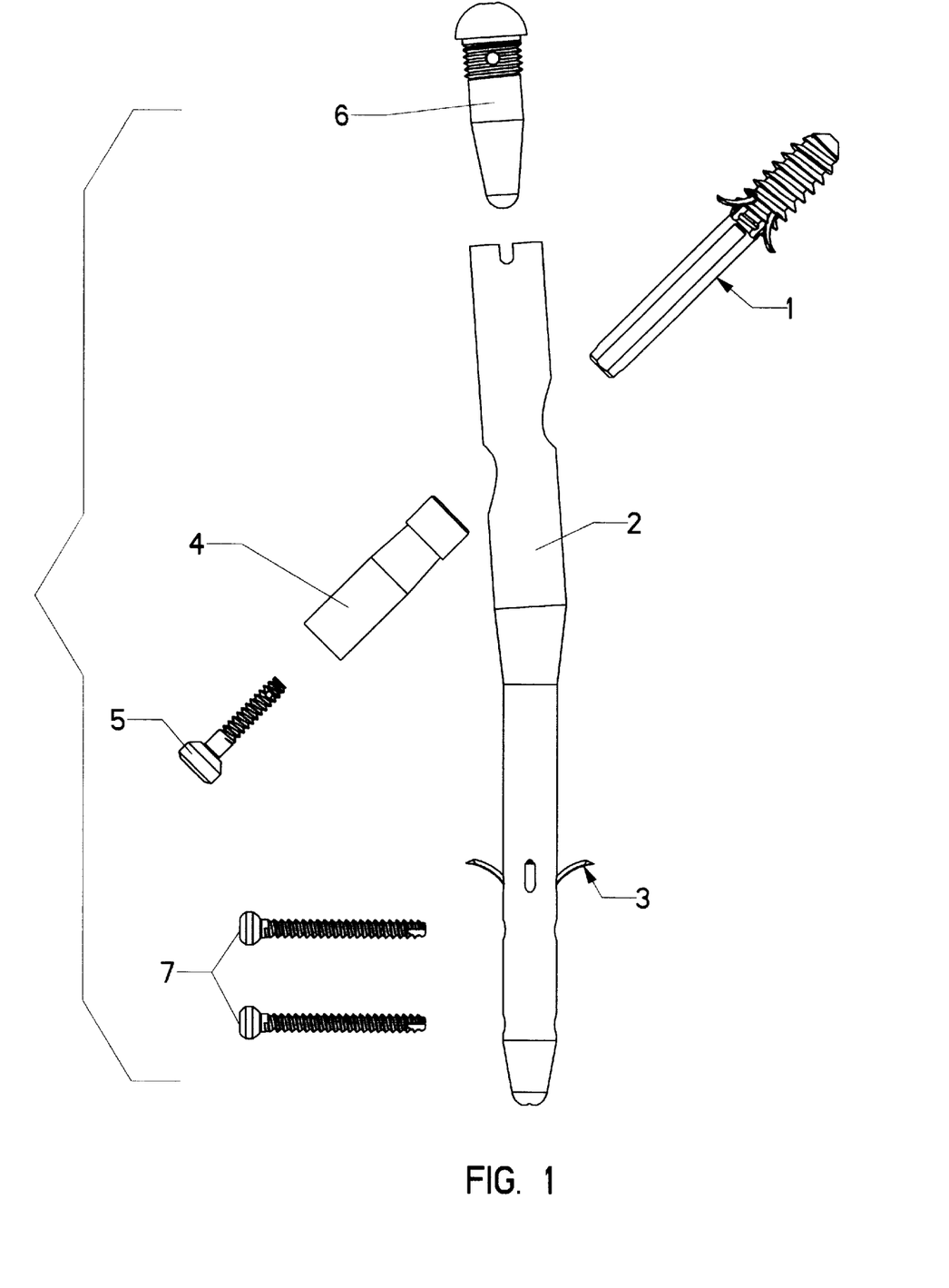
FIG. 1, is a longitudinal perspective view of the preferred embodiment intramedullary system in an exploded state.

The individual components of the assembly, as illustrated in FIG. 1, are constructed of implantable grade stainless steel alloys in the preferred embodiment but could also be constructed of implantable grade titanium alloys, as well. Other materials having the requisite properties, of strength and inertness, may be used. These components consist of the lag screw assembly 1, the nail body 2, the tang assembly 3, the sleeve 4, the compression screw 5, and the end cap 6 and the optional cortical screws 7.

Figures 2, 3:
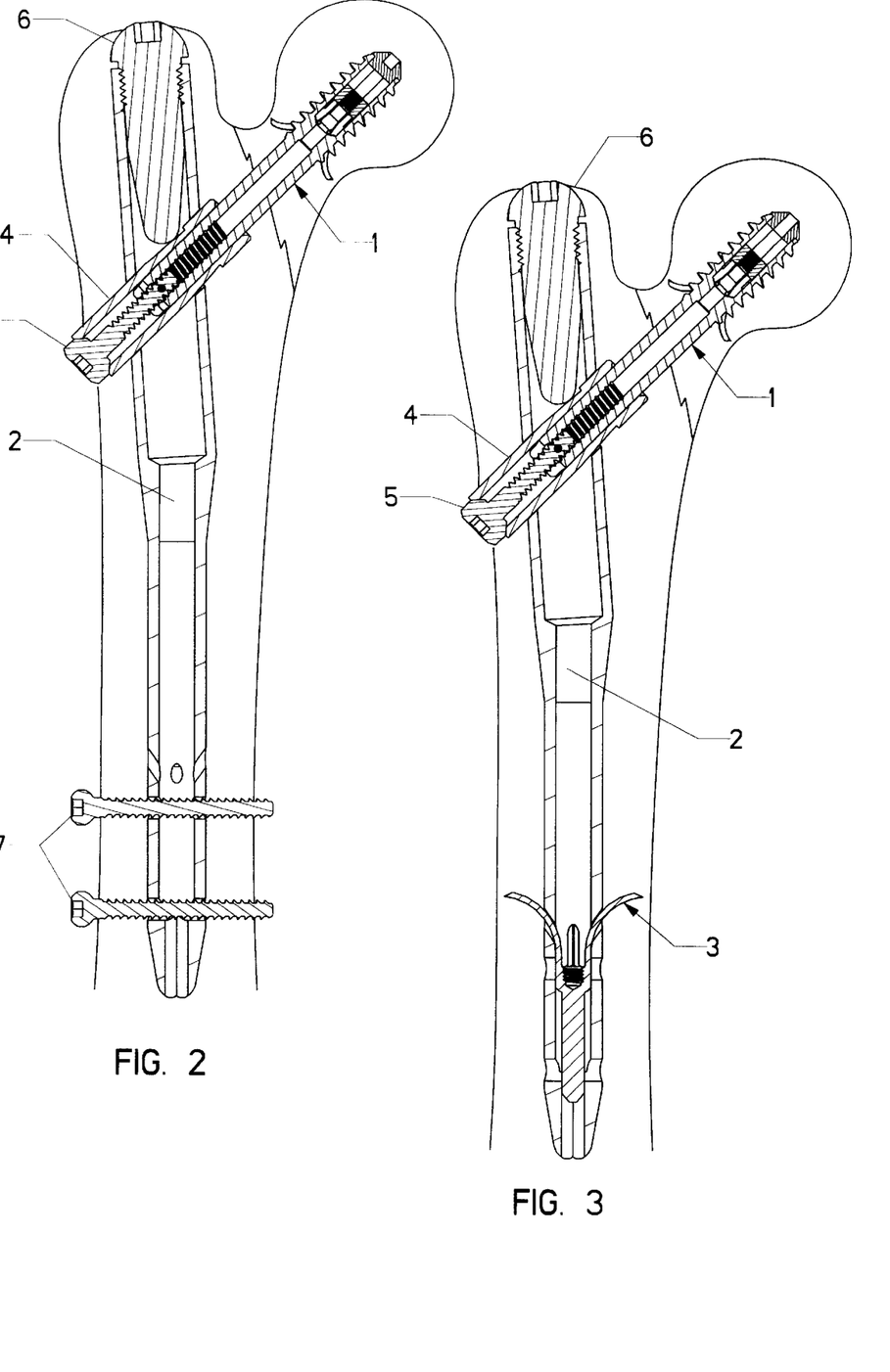
FIG. 2, is a view, partially in longitudinal cross section, of the intramedullary system placed in the intramedullary canal of a fractured bone using cortical screws as a method of fixation.
FIG. 3, is a view, partially in longitudinal cross section, of the intramedullary system placed in the intramedullary canal of a fractured bone using a tang assembly as a method of fixation.
Figure 5:
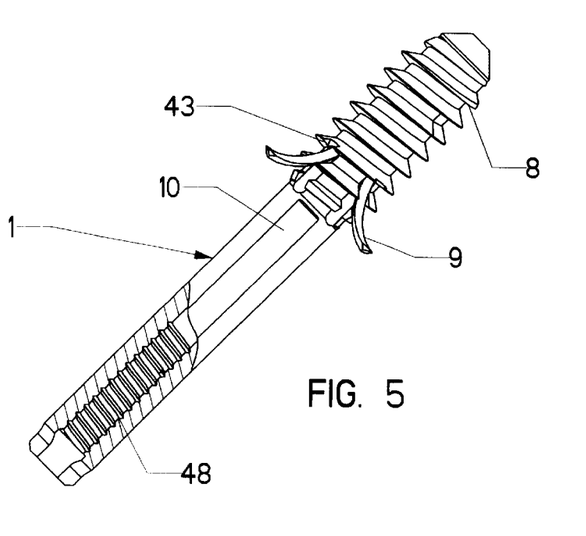
FIG. 5, is an enlargement of the lag screw assembly in FIG. 1.

The lag screw assembly 1 is described in detail in U.S. Pat. No. 6,183,474 B1, as is compression screw 5, and that disclosure is incorporated herein by reference. The external features of the lag screw assembly are indicated in FIG. 5. The threads 8 engage the cancellous bone within the femoral head on the medial or proximal side of the fracture line; the tang 9 is also located on the medial or proximal side of the fracture line as shown in FIG. 3. However, the tangs 9 are fully retracted into the body of the lag screw and remains that way until the lag screw assembly is fully positioned within the femoral head. When the tangs 9 are deployed through opening 43 into the femoral head, the tangs 9 penetrate the cortical bone, greatly increasing purchase (axial fixation) and rotational stability of the lag screw assembly. The tangs 9 are fully reversible if removal of the lag screw is ever required. As shown, the bone screw threads and the tangs are preferred, however either one of the structures may be used, alone, to attach the lag screw assembly to the bone. The shaft 10 is of a "double D" cross section which interfaces with bore 27 (FIG. 7B) and end configuration 31 (FIG. 7C) of the sleeve in such a way as to allow axial translation or slide of the lag screw while preventing rotation relative to the sleeve. This sliding prevents penetration of the femoral head by the proximal end of the lag screw as the fracture compresses from patient load bearing.

Figure 4A:
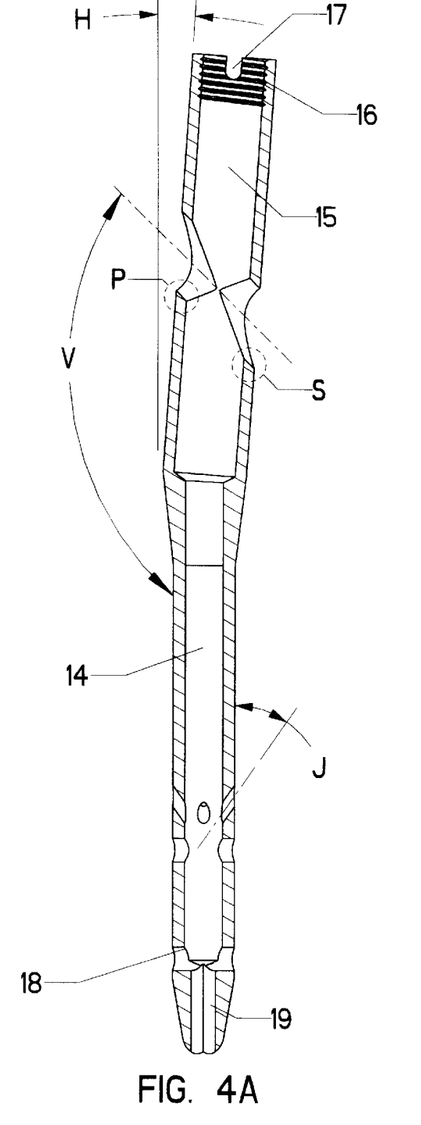
FIG. 4A, is an enlarged, cross section view of the intramedullary nail in FIG. 1.
Figure 4B:
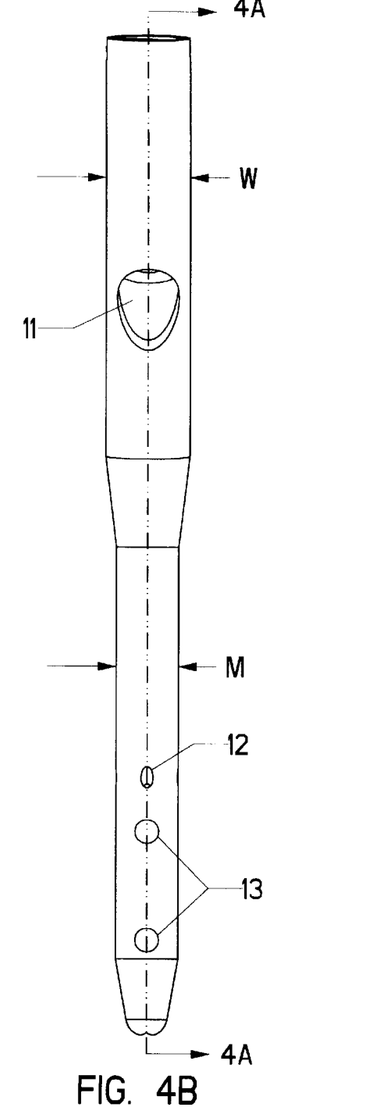
FIG. 4B, is a side view of FIG. 4A.
Figure 8A:
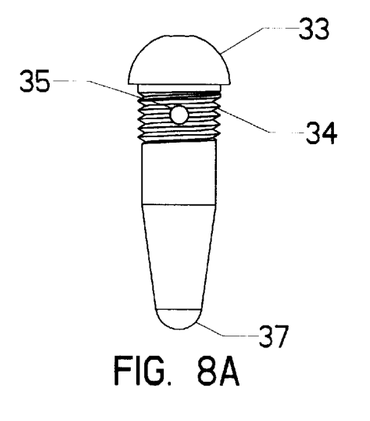
FIG. 8A, is an enlargement of the end cap in FIG. 1.
Figure 8B:
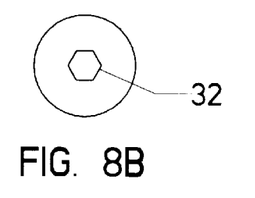
FIG. 8B, is a top view of FIG. 8A.
Figure 9A:
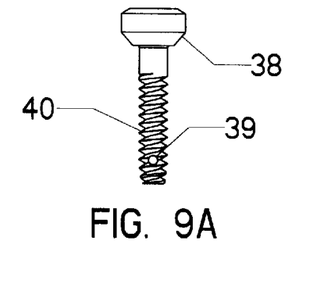
FIG. 9A, is an enlargement of the compression screw in FIG. 1.
Figure 9B:
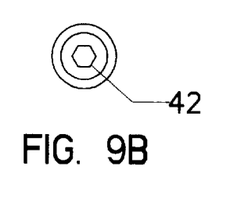
FIG. 9B, is a top view of FIG. 9A.

The nail body (FIGS. 4A, B, C) is designed for ante grade insertion into the intramedullary canal of the femur. It is anatomically shaped to the axis of the canal and has a medial to lateral bend angle H. The proximal outside diameter W of the body is greater than the distal outside diameter M due to narrowing of the canal and to allow the lag screw clearance radial bore 11 to be large enough to pass the threaded diameter 8 of the lag screw 1 and provide a sliding fit to the outside diameter L of the sleeve 4. The axis of clearance bore 11 is at an angle V with respect to the distal diametral axis. This angle V is such as to allow proper positioning of lag screw 1 within the femoral head. Both the proximal axial bore 15 and the distal axial bore 14 are of circular cross section. Distal bore 14 is sized to permit a sliding fit with the tang body 20. Four bores or tang portals 12 are located on a 90 degree radial spacing penetrating from the distal outside diameter M into the distal bore 14, on axes which form an angle J to the distal outside diameter M. This angle J is critical to the proper formation and exit of the tang 21. The clearance holes or bores 13 of FIG. 4B pass through the distal outside surface and wall into the distal bore 14 and continue on the same axis through the opposite wall and outer diameter. The clearance holes 13 are such as to allow passage of the threaded portion of the cortical screw 7 (FIG. 1). A frusto-conical feature 18 (FIG. 4A) provides a transition between the circular bore 14 and the square bore 19. The square bore 19 serves three purposes: it provides clearance through the distal end of the nail body 2 for passage of a guide pin, used during fracture alignment and installation of the of the nail body into the intramedullary canal, it provides a sliding fit for the square forward protrusion 23 (FIG. 6A) of tang assembly 3, and it acts as a "vent" hole forany organic material within the bore 14 which is being pushed ahead of the tang during tang installation. It must be noted that the forward most clearance holes 13 also intersect the frusto-conical feature 18 and will act as vents for organic material during tang insertion after the square protrusion 23 has engaged and filled square bore 19. The internal threads 16 at the proximal end of the nail body 2 provide for instrument interface, as do slots 17. The threads 16 are used for attachment and the slots 17 for radial alignment. The internal threads 16 also engage the external threads 34 (FIG. 8A) of end cap 6.

Figure 6A:
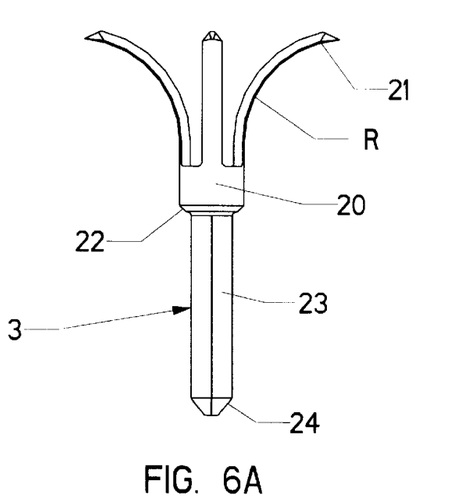
FIG. 6A, is an enlargement of the tang assembly in FIG. 3A.
Figure 6B:
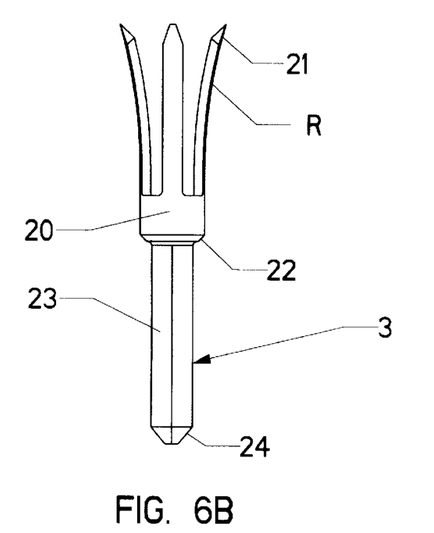
FIG. 6B, is an enlargement of the stowed tang assembly from FIG. 3B.
Figure 6C:
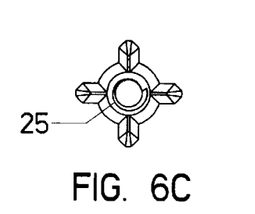
FIG. 6C, is a top view of FIG. 6B.

The tang assembly 3 has four equally sized and radially spaced tangs 21 which are preformed to radius R. The radius R (FIG. 6B) on each tang 21 results in a dimension between the trailing ends of opposing legs which is greater than the outside diameter of tang body 20 and the bore diameter 14 of nail body 2. The tang body 20 is circular in cross section and sized for a sliding fit within nail body bore1 4 with a leading edge chamfer 22 which transitions into the leading protrusion 23 which has a square cross section and leading end taper 24. Tang body 20 contains an internally threaded bore 25 which is the instrument interface for the instrument used to insert and deploy the tang. It must be noted that threaded bore 25 is not needed for tang retraction. FIG. 6A illustrates the deployed shape of tang assembly 3 which is the shape it assumes after the tangs 21 have been forced through the tang exit portals 12 of nail body 2.

Figure 3A:
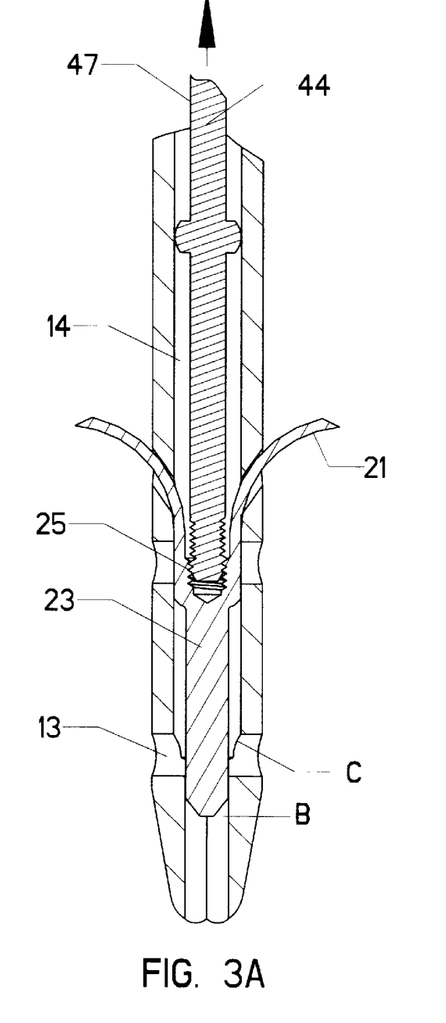
FIG. 3A, is an enlarged, cross section view of the tang assembly in FIG. 3.
Figure 3B:
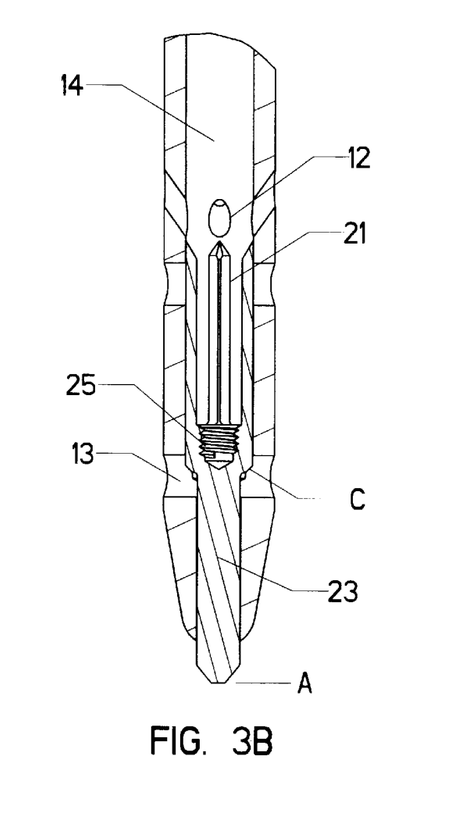
FIG. 3B, shows the stowed tang assembly from FIG. 3A.
Figure 3C:
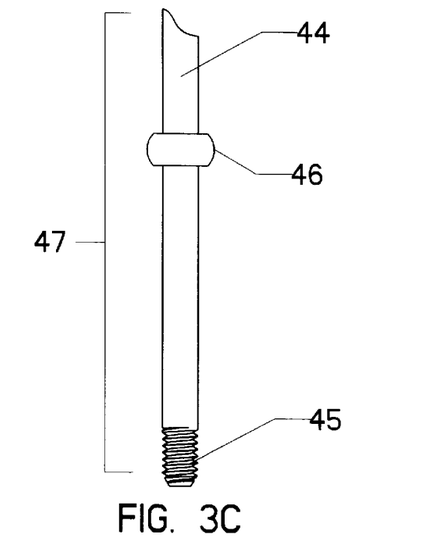
FIG. 3C shows the insertion/deployment/retraction instrument of FIG. 3A.

Insertion/deployment of the tang may occur after insertion of the nail body into the intramedullary canal. For tang assembly 3 insertion/deployment/retraction, the insertion/deployment/retraction instrument 47 (FIG. 3C) is employed. It has a shaft 44, one or more externally threaded end(s) 45 and guide 46. Shaft 44 is preferably circular in cross section with a diameter sized to allow reasonable flexibility or bending about the longitudinal axis as it travels through the nail body proximal bore 15 and distal bore 14 in order to follow the centerlines of both bores 14 and 15. The guide 46 provides a sliding fit in bore 14 and interacts with bore 14 in such a way as to center the shaft 44 within bore 14. Guide 46 also stabilizes shaft 44 in bore 14 to prevent shaft 44 from buckling under axial compressive load encounted during tang assembly retraction. The insertion/deployment instrument is threaded into tang-threaded bore 25. The tang is now inserted through nail body bore 15 and into nail body bore 14. Since the distance between opposing tang legs 21 is greater than the bore diameter 14 due to radius R, the interference with bore 14 forces the legs 21 inward in an elastic manner and insertion continues. As the tang assembly travels down bore 14, any organic material which has accumulated in bore 14 is pushed ahead and forced out through square bore 19 of nail body 2 and through clearance holes 13. Further insertion causes the tang assembly 3 leading square taper 24 to contact the square bore 19 of the nail body 2. Since both cross sections are square, no engagement will occur until they are radially aligned which may or may not occur without some slight rotation of the tang assembly 3 using the insertion/deployment instrument. After alignment occurs and by virtue of this alignment, the tang leading protrusion 23 will slide freely in square bore 19 and the tangs 21 and the nail body 2 tang portals 12 will now be aligned. The tang 3 continues past tang exit holes 12 and is fully inserted when the tang body leading edge chamfer 22 makes contact with the nail body frustroconical feature 18 at point C of FIG. 3B. In this position, the tang leading protrusion 23 protrudes through the end of nail body 2 to point A and the trailing end of the tangs 21 are just past tang portals 12. The tangs are now in position to be deployed. To deploy the tangs, an axial force is exerted by the insertion/deployment/retraction instrument 47 in the opposite direction as for insertion. This causes the tang assembly 3 to translate back up bore 14 and the sharp ends of tangs 21 to encounter tang portals 12. Since the tangs 21 were elastically compressed inward by bore 14 they will now spring outward forcing the sharp end of tang legs 21 into tang exit holes 12. Further translation of the tang assembly 3 forces the tang legs through the tang exit holes 12. Due to the diameter and angle of the tang portals 12, the tangs 21 are formed in such a manner as to emerge almost perpendicular to the femoral cortex. Continued translation of the tang assembly 3 causes the tangs 21 to penetrate the femoral cortex. During this time, tang leading square protrusion 23 is still engaged by the nail body square bore 19 thus preventing rotation of tang assembly 3 in bore 14 during deployment and preventing unwanted twisting of the tangs 21. The tang assembly 3 can be deployed fully or partially and is self locking in any position due to the almost perpendicular entry angle into the cortex. After deployment, the insertion/deployment/retraction instrument is unthreaded from tang threaded bore 25 and removed. The nail body 2 is now fixed axially and rotationally in the intramedullary canal. FIG. 3A shows the tang assembly 3 in the fully deployed position having translated a distance from point A in FIG. 3B to point B of FIG. 3A. The tangs 21 are fully retractable. They are retracted by applying a force on the tang assembly 3 with the insertion/deployment/retraction instrument 47 in the opposite direction as deployment (opposite of arrow direction in FIG. 3A) until the tang assembly 3 comes to rest at points C and A in FIG. 3B.

Distal fixation of the nail body 2 can be accomplished without use of tang assembly 3. This is accomplished by using the cortical screws 7 (FIG. 1 and FIG. 2). The cortical screws 7 are placed through the lateral femoral cortex and through clearance holes 13 in the nail body 2, then through the medial femoral cortex as shown in FIG. 2. The cortical screws are not used in conjunction with distal tang fixation and cannot be passed through clearance holes 13 if there is a tang assembly 3 inserted into nail body 2.

Figure 4C:
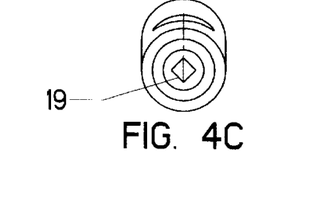
FIG. 4C, is an end view of FIG. 4B.
Figure 7A:
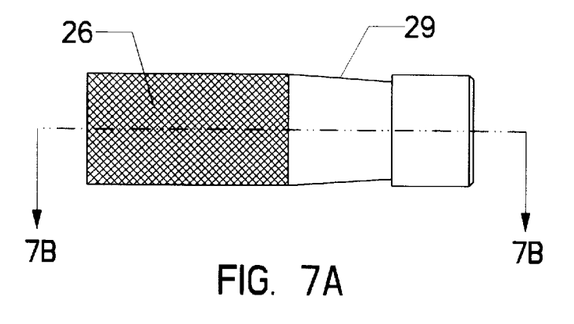
FIG. 7A, is an enlargement of the sleeve in FIG. 1.
Figure 7B:
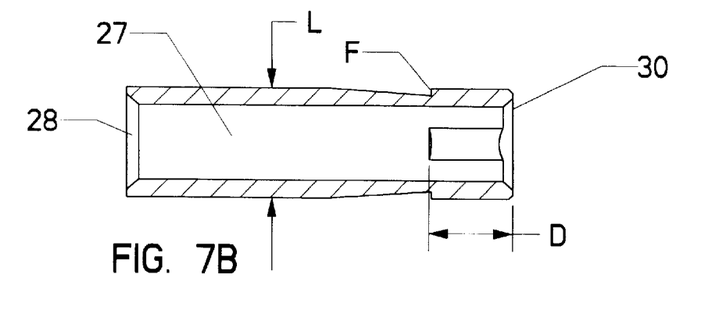
FIG. 7B, is a cross section view of FIG. 7A.
Figure 7C:
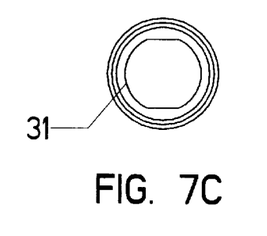
FIG. 7C, is an end view of FIG. 7A.

Sleeve 4 is utilized to secure lag screw assembly 1 into clearance bore 11 after implantation of the lag assembly 1 and nail body 2 in the femur. The outside diameter L (FIG. 7B) is sized for a sliding fit in bore 11. The sleeve 4 has a circular bore 27 and a small length (D) of "double D" bore 31 at the leading end. The leading bore also contains a countersink 30. Between the leading and trailing ends is a tapered cross section 29. The trailing outside diameter has a diamond knurl 26 and the circular bore 27 contains a countersink 28 at the trailing end. After the lag screw 1 is in position its trailing end protrudes partially or fully through nail body 2 bore 11. The leading end of sleeve 4 containing bore 31 is inserted into bore 11 and the bore 31 aligned with the similarly shaped lag screw shaft 10. The sleeve 4 is inserted further into bore 11 thus mating, with the aid of countersink 30, the sleeve 4 and lag screw shaft 10. The sleeve 4 is placed within bore 11 such that the leading end of taper 29 or shoulder F in FIG. 7A is located property with respect to bore 15 of nail body 2 (FIGS. 2 and 3). The end cap 6 is inserted into the proximal end of nail body 2 until external threads 34 (FIG. 8A) contact the internal threads 16 of nail body 2. The end cap 6 is then rotated clockwise by means of hexagonal recess 32 to engage the threads. End cap 6 contains a patch of ultra high molecular weight polyethylene 35 which acts as a thread locking element to help prevent unwanted loosening of end cap 6. As the end cap advances its leading end spherical radius 37 contacts sleeve taper 29 forcing sleeve 4 against the opposite side of bore 11 indicated P (FIG. 4C). At this time the taper 29 is in contact with one end of bore 11 and the knurl surface 26 is in contact with the opposite end of bore 11, indicated S in FIG. 4C. The taper 29 interaction with end cap spherical radius 37 prevents any translation of sleeve 4 in bore 11 in the direction of the lag screw and interaction of the end cap spherical radius 37 with the sleeve taper shoulder F prevents translation of the sleeve in the opposite direction.

Interaction of knurled surface 26 of sleeve 4 and bore 11 in conjunction with interaction of end cap spherical radius 37 and sleeve 4 taper 29 prevents rotation of sleeve 4 in bore 11. Sleeve 4 is now fixed in translation and rotation. Therefore, lag screw 1 is now fixed in rotation but free in axial translation.

With the lag screw 1 fixed to one side of the fracture and the nail body 2 and sleeve 4 affixed to the other, the compression screw 5 can be utilized to draw the two assemblies together and compress the fracture. The externally threaded end 40 of the compression screw 5 is inserted through the trailing end of sleeve 4 and mated with the internal threads 48 in the trailing end of lag screw 1. Advancing the screw utilizing drive recess 42 the threads engage. An ultra high molecular weight polyethylene patch 39 in the compression screw thread 40 provides thread locking. As the threads further engage, compression screw chamfer 38 contacts sleeve 4 countersink 28 causing lag screw 1 to be drawn towards nail body 2 as the compression screw 6 is further rotated thus compressing the fracture.

It is to be understood that while we have illustrated and described certain forms of the invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. An intramedullary system having a lag screw assembly in combination with an intramedullary nail, for implantation in the intramedullary canal of a long bone, said intramedullary nail comprising an elongated body with a proximal end and a distal end, said proximal end having at least one radial bore, said lag screw assembly extending through said radial bore an adjustable distance, said lag screw assembly and said intramedullary nail including cooperating structure for adjusting and fixing said distance, wherein said distal end has a plurality of radial bores disposed therein, an anchoring device is adapted to be disposed in at least one of said plurality of radial bores and wherein said elongated body is cannulated with an axial bore at said proximal end and an axial bore at said distal end, said anchoring device disposed in said axial bore at said distal end, said anchoring device including at least one tang adapted to extend through at least one of said plurality of radial holes.

2. An intramedullary system of claim 1 wherein said leading end of said lag screw assembly includes external bone screw threads for fixed engagement in said bone.

3. An intramedullary nail of claim 1 wherein said leading end of said lag screw assembly includes an internal tang and an aperture, said tang adapted to extend through said aperture for fixed engagement in said bone.

4. An intramedullary system of claim 3 wherein said leading end of said lag screw assembly includes external bone screw threads for fixed engagement in said bore.

5. An intramedullary system of claim 1 wherein said structure for securing said trailing end of said lag screw to said intramedullary nail comprises screw threads on said trailing end of said lag screw and a compression screw adapted for cooperating therewith.

6. An intramedullary system of claim 1 wherein an axial bore extends from said radial bore through said proximal end, an end cap securely fastened in said axial bore frictionally contacting said structure for securing said trailing end of said lag screw assembly.

7. An intramedullary system of claim 6 wherein said structure for securing said trailing end includes a sleeve surrounding said trailing end and disposed in said radial bore, said trailing end slidable within said sleeve, said end cap frictionally contacting said sleeve and securing said sleeve in said radial bore.

8. An intramedullary system of claim 7 wherein said structure for securing said trailing end includes screw threads on said trailing end and a compression screw inserted within said sleeve and cooperating with said screw threads to apply compression between said sleeve and said leading end of said lag screw assembly.

9. An intramedullary system comprising a lag screw assembly in combination with an intramedullary nail, said lag screw assembly and said intramedullary nail sized and shaped for insertion into a long bone, said intramedullary nail having a proximal end with an axial bore, a distal end with an axial bore, said axial bores extending from said proximal end through said distal end, said proximal end having a radial bore, said lag screw assembly adapted to adjustably traverse said radial bore, said distal end having at least one radial bore, a tang assembly slidably disposed in said distal end of said axial bore, said tang assembly having at least one tang adapted to extend through said at least one radial bore in said distal end whereby sliding movement of said tang assembly extends said tang through said radial bore.

10. An intramedullary system of claim 9 wherein said at least one tang is curved in the extended position.

11. An intramedullary system of claim 9 wherein said distal end has a plurality of radial bores and said tang assembly has a plurality of tangs adapted to extend through said plurality of radial bores.

12. An intramedullary system of claim 9 wherein said axial bore of said proximal end of said intramedullary nail and said axial bore of said distal end intersect at an angle approximating anatomical shape.

13. An intramedullary system of claim 12 wherein an insertion/deployment/retraction instrument is slidably disposed in said proximal axial bore and said distal axial bore, said instrument connected to said tang assembly whereby manipulation of said instrument slidably moves said tang assembly and deploys said tangs.

14. An intramedullary system of claim 12 wherein said radial bore in said proximal end has an axis, said axis of said radial bore intersecting said axial bore of said proximal end at an angle to allow proper positioning of said lag screw assembly in said bone.

15. An intramedullary system kit comprising a lag screw assembly, an intramedullary nail, a tang assembly with resilient tangs, cortical screws, a sleeve, a compression screw, an end cap and an insertion/deployment/retracion instrument, said lag screw assembly having a leading end and a trailing end, said leading end having attachment means for connecting said leading end to a portion of a bone, said intramedullary nail having a proximal end and a distal end, an axial bore through said proximal end and said distal end, a radial bore in said proximal end, and a plurality of radial bores in said distal end, said tang assembly slidably disposed in said axial bore of said distal end, said instrument disposed in said intramedullary nail proximal axial bore and distal axial bore and connected to said tang assembly, said instrument adapted to slide said tang assembly to deploy said tangs through said radial bores in said distal end into said bone, said cortical screws adapted to be inserted through said radial bores in said distal end, said radial bore in said proximal end sized to permit passage of said leading end of said lag screw assembly, said lag screw assembly adapted to extend through said radial bore in said proximal end with said trailing end disposed in said axial bore, said sleeve sized to extend through said radial bore in said proximal end and slidably surround said trailing end of said lag screw assembly, said end cap adapted for connection with said axial bore in said proximal end of said nail and engage said sleeve for fixing said sleeve in said radial bore, said compression screw adapted to be connected with the trailing end of said lag screw assembly and said radial bore of said proximal end whereby manipulation of said compression screw will apply compression between said intramedullary nail and said lag screw assembly.

16. A method of fixing portions of a bone together comprising the steps of providing an intramedullary system having a lag screw assembly for adjustable connection to an intramedullary nail by a compression screw, said intramedullary nail having a proximal end with an axial bore, a distal end with an axial bore, a radial bore in said proximal end, and a plurality of radial bores in said distal end, said lag screw assembly sized to traverse said radial bore in said proximal end, a cap screw in said axial bore of said proximal end, said cap screw for frictionally engaging and securing said lag screw assembly in said radial bore, an anchoring device disposed in said axial bore of said distal end, wherein said anchoring device further comprises a tang assembly slidably disposed in said axial bore of said distal end, said tang assembly having resilient tangs for traversing said radial bores in said distal end and engaging said portion of bone and an instrument for sliding said tang assembly inserting said intramedullary nail in said intramedullary canal of a portion of the bone, traversing said anchoring device through said radial bore in said proximal end, traversing said lag screw assembly through said radial bore is said proximal end, deploying said lag screw in another portion of the bone, inserting said instrument through said proximal end axial bore and said distal end axial bore to connect with said tang assembly, manipulating said instrument to slide said tang assembly to cause said tangs to traverse said radial bores and engage said portion of said bone removing said instrument, inserting said cap screw in said axial bore of said proximal end, and adjustably connecting said lag screw assembly and said intramedullary nail with said compression screw to gain compression between said lag screw assembly and said intramedullary nail.

\* \* \* \* \*